(12) United States Patent
Frings et al.

(10) Patent No.: US 8,672,956 B2
(45) Date of Patent: Mar. 18, 2014

(54) ENDOSCOPIC SUTURING MACHINE (75) Inventors: Hermann-Josef Frings, Aachen (DE); Manfred Krings, Aachen (DE); Gunter Moik, Aachen (DE)

(73) Assignee: KARL STORZ-Medizinische Nähsysteme GmbH & Co., KG, Tuttlingen (DE)

( * ) Notice: Subject to any disclaimer, the term of this patent is extended or adjusted under 35 U.S.C. 154(b) by 156 days.

(21) Appl. No.: 13/109,267

(22) Filed: May 17, 2011

(65) Prior Publication Data

US 2011/0288564 A1 Nov. 24, 2011

(30) Foreign Application Priority Data

May 18, 2010 (DE) .......................... 10 2010 021 273

(51) Int. Cl.
*A61B 17/04* (2006.01)
(52) U.S. Cl.
USPC .......................................................... 606/145
(58) Field of Classification Search
USPC ................................................ 606/144–147
See application file for complete search history.

(56) References Cited

U.S. PATENT DOCUMENTS 4,440,171 A * 4/1984 Nomoto et al. ............... 606/145

FOREIGN PATENT DOCUMENTS

DE 101 16 171 A1 10/2002

* cited by examiner

*Primary Examiner* — Gregory Anderson
(74) *Attorney, Agent, or Firm* — McGlew and Tuttle, P.C.

(57) ABSTRACT

An endoscopic suturing machine, having a housing with a housing upper part for receiving drives for the stitch-forming tools, a housing shaft adjoining the housing upper part for a receiving device for transmitting the motions generated by the drives to the stitch-forming tools, which have at least one needle bar guided in the housing shaft with a thread-carrying needle and a shuttle cooperating with same for forming stitches. The shuttle is received by a shuttle bar. The needle bar (5) is designed as a hollow body for receiving and guiding the thread. The thread guide elements are arranged between the thread spool 31 receiving the thread reserve and the needle bar (5) and are arranged in relation to the needle bar (5) such that the thread runs essentially in a straight line between the exit from the mounting device (17) and the entry into the needle bar (5).

20 Claims, 5 Drawing Sheets

ENDOSCOPIC SUTURING MACHINE

CROSS REFERENCE TO RELATED APPLICATIONS

This application claims the benefit of priority under 35 U.S.C. §119 of DE 10 2010 021 273.3 filed May 18, 2010, the entire contents of which are incorporated herein by reference.

FIELD OF THE INVENTION

The present invention pertains to an endoscopic suturing machine with a means for supplying and guiding the thread.

BACKGROUND OF THE INVENTION

DE 101 16 171 A1 discloses an endoscopic suturing machine with a housing, which is essentially formed by a housing upper part used to receive drives for the stitch-forming tools and a housing shaft adjoining same, which said shaft receives the means for transmitting the motions generated by the drives to the stitch-forming tools.

These comprise at least one thread-carrying needle received by a needle bar and a shuttle, which cooperates with same to form stitches and is received by a shuttle bar.

The question of supplying and feeding the thread from a thread reserve to the eye of the needle is addressed in DE 101 16 171 A1 just as little as the question of setting the value of the thread tension necessary for forming the individual stitches. This is also understandable insofar as by integrating these means in an endoscopic suturing machine, these would become substantially m ore complicated and hence also substantially more error-prone. However, this is precisely what shall be avoided in light of the fact that endoscopic suturing machines are used mainly within the human or animal body and shall therefore be extremely reliable.

The endoscopic suturing machine according to DE 101 16 171 A1, which forms a so-called "single-thread overedge seam," uses a shuttle, which can be moved, after grasping the thread loop formed by the needle on the underside of the material being sutured, along a multidimensional path of motion from the position that is located under the material being sutured and grasps the thread loop into a position, which is located above the material being sutured and in which the thread triangle formed by the thread loop being led to the top side of the material being sutured encloses the projection of the needle path.

Due to the frequent change in the direction of thread motion from leaving the thread reserve to the insertion of the needle into the thread triangle formed by the shuttle on the top side of the material being sutured, the thread passes through a plurality of deflection sites equaling up to 180°, which leads to a considerable multiplication of the tensile force acting in the thread. As a result, both the needle bar and especially also the shuttle bar receiving the shuttle are exposed to a radial load, which is a multiple of the thread retention force needed for pulling in the stitch. However, these loads, especially of the shuttle bar, therefore lead in a very short time to deformations of the needle bar and especially of the shuttle bar, which are very often the cause of formation of missed stitches.

SUMMARY OF THE INVENTION

A basic object of the present invention is therefore to minimize the thread forces acting on both the shuttle bar and the needle bar and to increase the safety of stitch formation.

The present invention is based for this on the discovery that the thread retention force necessary in the area of the thread tensioning means is composed essentially of two components, namely, the value of the thread pull-in force proper necessary for the suturing technique and the frictional forces to be overcome to overcome the thread friction from the stitch formation site to the thread tensioning means.

A basic object of the present invention is therefore to select the course of the thread from the stitch formation site to the thread tensioning means such that the thread friction forces are extensively minimized.

This object is accomplished according to the present invention by the needle bar for receiving and guiding the thread being designed as a hollow body, and by the thread tensioning means being arranged in relation to the needle bar such that the thread runs essentially in a straight line between the thread tensioning means and its entry into the needle bar.

It is achieved by the measure of designing the needle bar as a hollow body receiving the thread and of arranging the thread tensioning means in relation to the needle bar such that the thread runs essentially in a straight line between the thread tensioning means and its entry into the needle bar that the thread retention force to be applied by the thread tensioning means must be dimensioned only slightly stronger than the stitch pull-in force necessary to guarantee the pulling in of the stitch. Since the design of the needle bar according to the present invention as a hollow body offers the possibility of leading the thread out of the needle bar optionally on the side or on the front side, all the hitherto necessary deflections are eliminated for the thread between the entry into the needle bar and its exit from the needle bar, so that the frictional forces that will still come to act can be reduced to an extremely low minimum.

An especially simple guide for the thread, which has a smooth guide surface, can be obtained within the needle bar by using a guide element arranged within the hollow needle bar, which said element preferably consists of a plastic.

As an alternative to the front-side exit of the thread from the needle bar, a lateral exit can be obtained by the needle bar having, in the area of the fastening means for the needle, an outwardly and preferably obliquely downwardly directed outlet opening for the thread.

If the needle used is a needle provided with a thread slot and a flat shank, both guiding and protection of the thread from external effects can be achieved if the longitudinal groove forms, together with the thread slot of the needle, a thread duct and the thread exits from the thread duct on the front side of the thread duct.

In another embodiment of the present invention, the needle may be designed as a cannula, in which case it is advantageous for increasing the reliability of grasping the thread loop by the tip of the shuttle if the cannula has a lateral recess for the tip of the shuttle to reduce the lateral distance between this and the path of motion of the tip of the shuttle in the rest of the area of the needle eye. The cannula may have an oblique polished section, as a result of which an oval exit opening directed to the side is formed for the thread.

The measure of mounting the thread reserve within a mounting device and of detachably connecting this to the needle bar, for example, by means of a screw connection, leads to a relatively short and deflection-free thread path, on the one hand, and offers, on the other hand, the possibility of sterilizing at first the needle bar and the empty mounting device together and of storing these as a ready-to-use assembly unit after threading the needle and of inserting these in the machine as an assembly unit when needed.

It is advantageous for the use of prefilled thread spools to form the mounting device for the thread reserve from a two-part housing and to provide the base part thereof with a cylindrical mount as well as with a centering pin for the thread spool.

Stiffness of the thread spool during the pulling off of the thread can be prevented by forming at the centering pin a contact surface for the thread spool, which has an axial distance from the bottom surface of the mount.

In order not to have to always detach the drive connection of the needle bar with the connecting rod moving same each time the needle bar is replaced within the framework of a kind of disassembly of the machine, the needle bar is arranged within a sleeve driven by the connecting rod and is detachably connected to same. The motion of the connecting rod is derived in this case from the main shaft of the machine. The sleeve is connected for this to the connecting rod via a usual revolute joint, while the connection between the needle bar and the sleeve is established by means of a detachable quick connection. This may be formed in a simple and reliable manner by a bayonet catch, whose fixed part is connected to the sleeve and whose loose part is connected to the needle bar. The needle bar can thus be removed from the machine practically with very little effort and reinserted into the machine just as easily.

The fixed part of the bayonet catch is adjusted relative to the hinge point between the connecting rod and the sleeve for both the radial and axial adjustment of the needle bar. The hinge point may be designed for this between the connection rod and the sleeve as a clamping device for receiving the sleeve.

To protect both the thread reserve and the area of the thread leading from the thread spool to the needle bar from external effects, the thread tensioning means is also arranged within the mounting device in addition to the thread reserve.

A simple design for the thread tensioning means is obtained by this being formed essentially by two pressure pieces arranged in parallel to one another and one on top of another, the upper pressure piece lying on the lower pressure piece in a non-positive manner, and by an adjusting means, whose handle projects from the mounting device, being associated with the spring bringing about the frictional connection for changing the pressing force.

Further details and advantages of the present invention appear from the following description of an exemplary embodiment of the present invention shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figures 1, 1A:
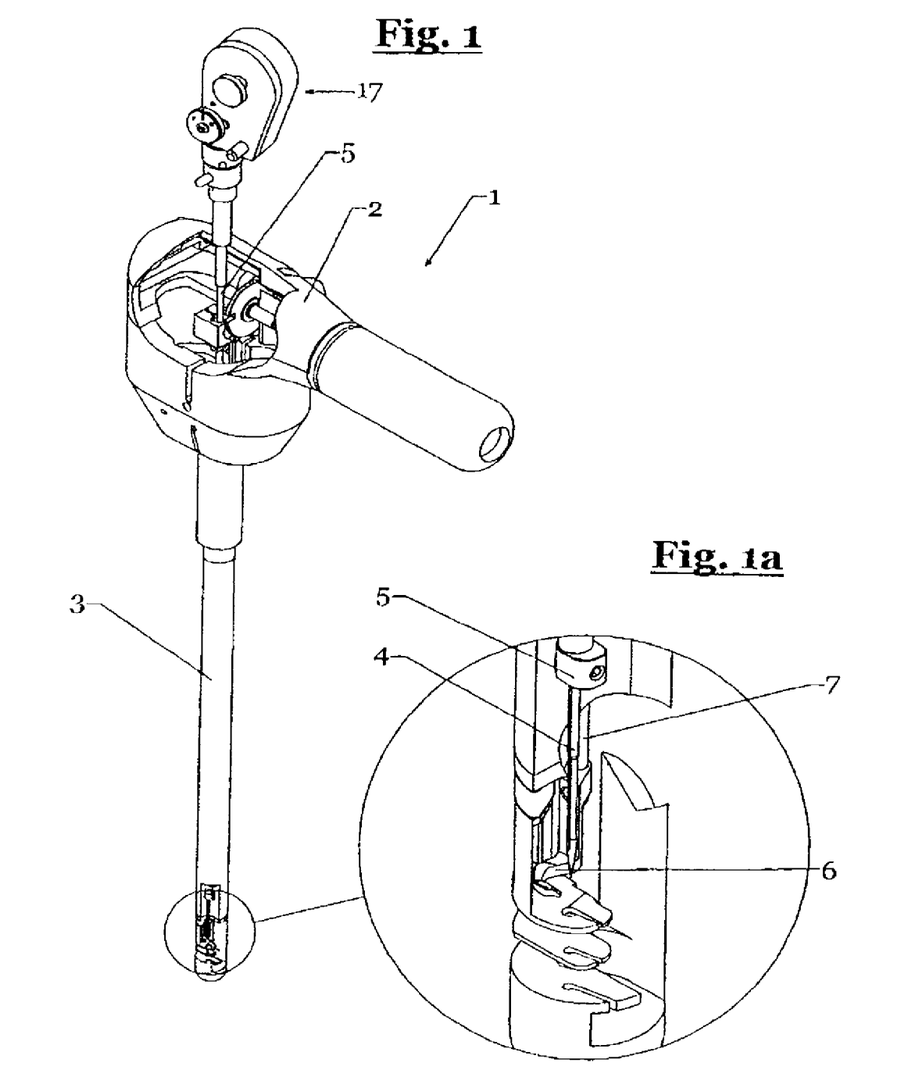
FIG. 1 is a schematic view of an endoscopic suturing machine.
FIG. 1a is an enlarged view of the stitch formation area in FIG. 1.

Referring to the drawings in particular, FIG. 1 schematically shows a housing 1 of an endoscopic suturing machine, which housing has a housing upper part 2 for receiving drives for the stitch-forming tools, as well as a housing shaft 3 adjoining the housing upper part for receiving transmission means for transmitting the motions generated by the drives to the stitch-forming tools. These stitch-forming tools comprise essentially a needle 4 carrying a thread, a needle bar 5 receiving same, as well as a shuttle 6, which cooperates with the needle 4 to form stitches and is received by a shuttle bar 7. The shuttle bar 7 is mounted displaceably and rotatably in the housing shaft 3, so that after grasping the thread loop formed by the needle 4 on the underside of the material being sutured, the shuttle 6 can be moved along a multidimensional motion path from the position located under the material being sutured, which grasps the thread loop, into a position located above the material being sutured, in which position the thread triangle formed by the thread loop led to the top side of the material being sutured encloses the projection of the needle path.

The general design of the stitch-forming tools and the mode of action thereof may correspond to the mode of action of the endoscopic suturing machine according to DE 101 16 171 A1 (corresponding U.S. Pat. No. 7,354,443 is hereby incorporated by reference in its entirety), which is used to form an overedge seam with the use of a type of stitch corresponding to stitch type 501.

To avoid more thread from being pulled in from the thread reserve during the pulling in of the stitch, a thread tensioning means 8 (FIGS. 2, 3) is provided, whose retaining force for the thread is stronger than the thread pull-in force.

Figure 2:
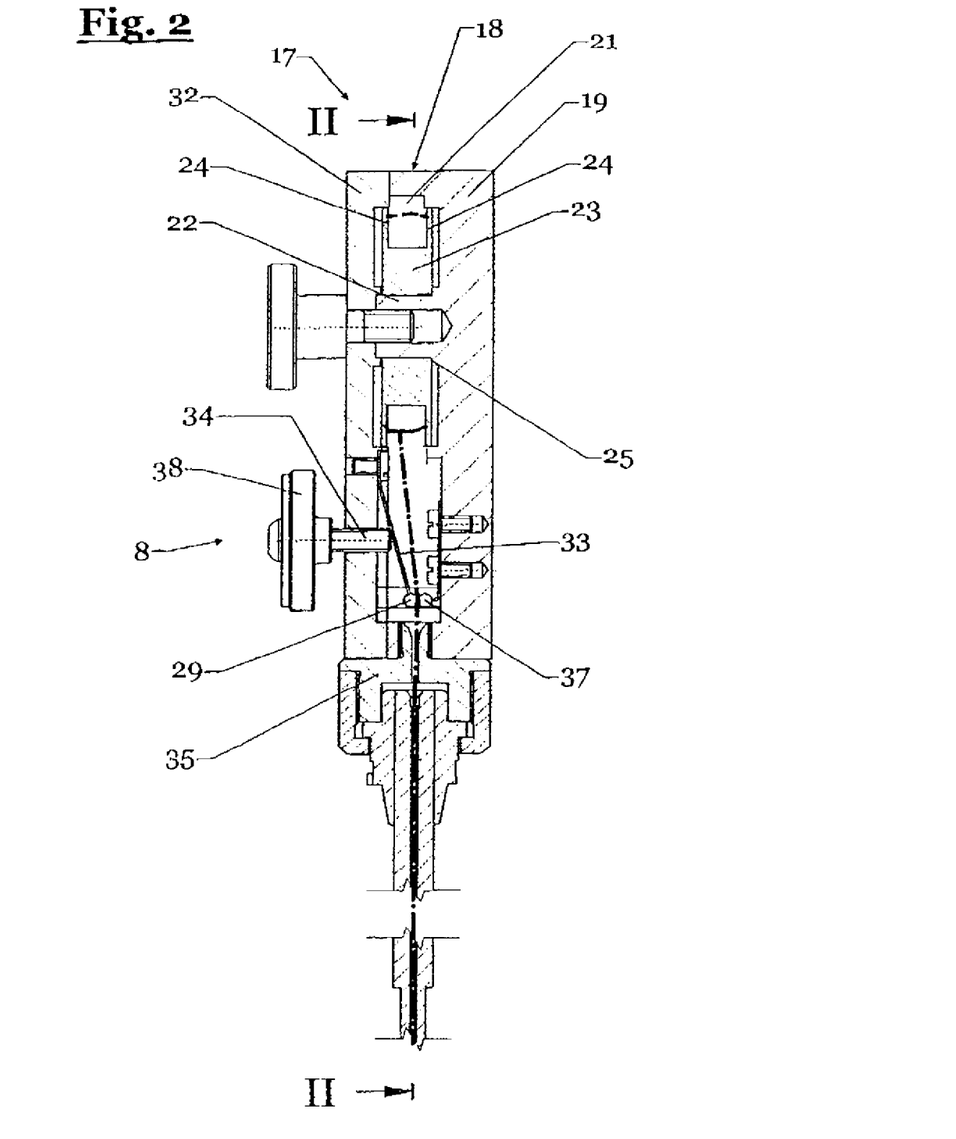
FIG. 2 is a sectional view of the mounting device for the thread reserve and thread tensioning means.
Figures 3, 3A, 4:
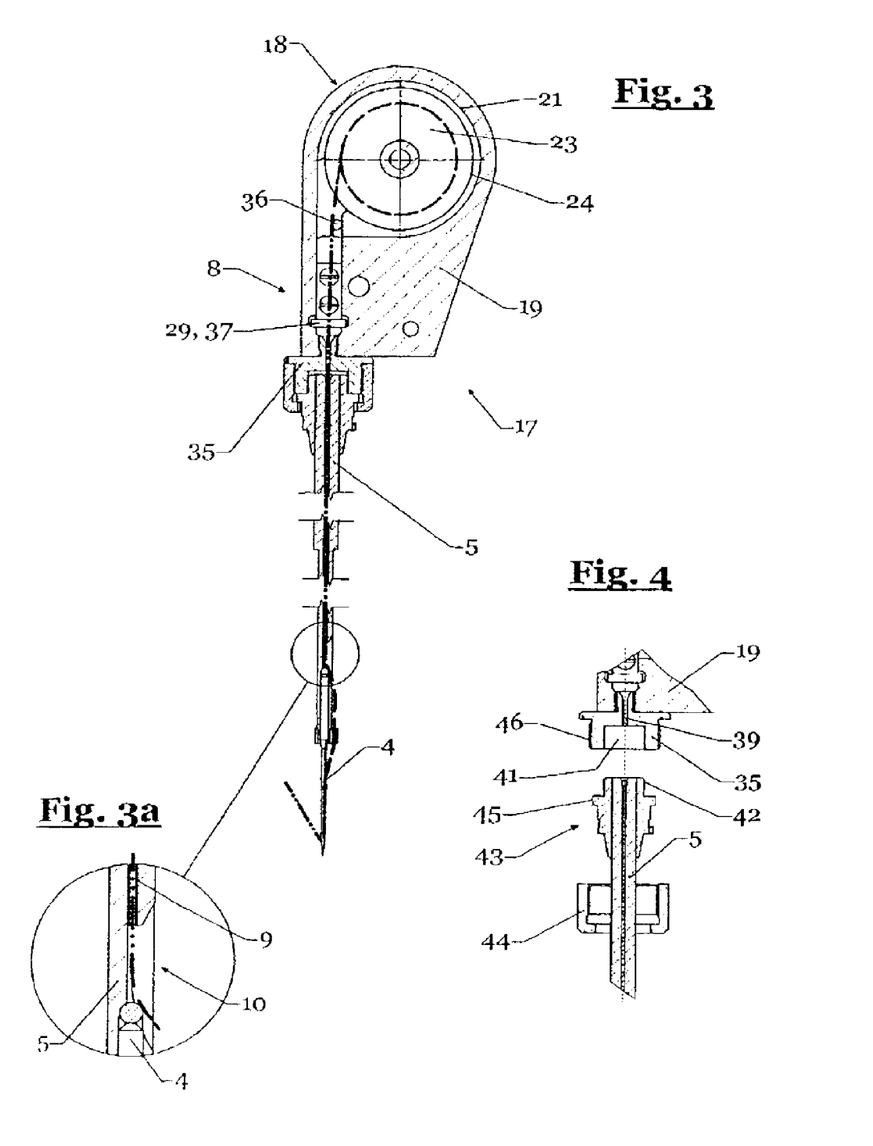
FIG. 3 is a section along line II-II in FIG. 2.
FIG. 3a is an enlarged view of the area of the outlet opening of the needle bar.
FIG. 4 is a sectional view of the connection area of the needle bar with the mounting device for the thread reserve and thread tensioning means.

The needle bar 5 is designed as a hollow body for receiving and guiding the thread. The thread tensioning means 8 is arranged in relation to the needle bar 5 such that the thread runs essentially in a straight line between the exit from the thread tensioning means 8 and the entry into the needle bar 5.

Since all the thread deflections that have hitherto been present on the way of the thread from the thread reserve to the needle 4 are eliminated by this relative position of the thread tensioning means 8 in relation to the needle bar 5 designed as a hollow body, the frictional resistance for the thread decreases, on the one hand, and the needle bar 5 assumes, together with the needle 4, the function of the hitherto necessary thread lever, on the other hand.

A guide element 9 (FIG. 3a) for the thread, which passes through the needle bar 5 and which preferably has a tube-like design and may be made of plastic, is arranged within the needle bar 5. Furthermore, an outwardly and preferably obliquely downwardly directed cross hole, which acts as an exit opening 10 for the thread from the needle bar 5, is provided at the needle bar 5 in the area of the usual fastening means for the needle 4.

As an alternative to this, the needle bar 5 may have a longitudinal groove 11 (FIGS. 5, 5a, 5b) for receiving the thread in the area of the fastening means for the needle 4.

Figures 5, 5A:
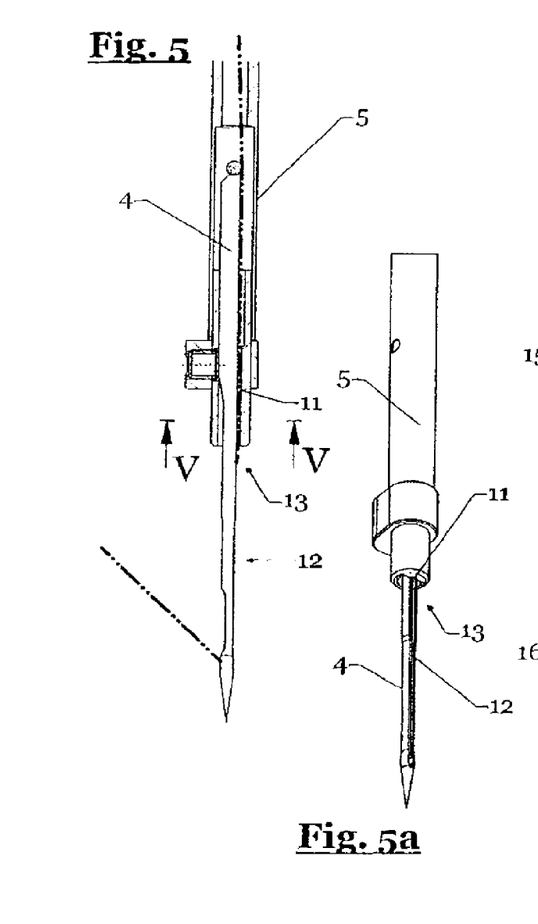
FIG. 5 is a sectional view of a first embodiment of the needle bar and needle.
FIG. 5a is a front view of the first embodiment of the needle bar and needle.
Figure 5B:
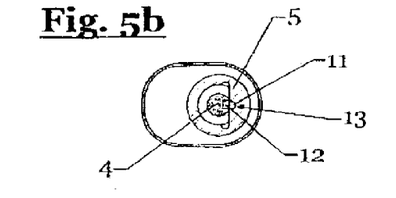
FIG. 5b is a section along line 5-5 in FIG. 5.

If a needle 4 provided with a flat shank and with a thread slot 12 is used, the longitudinal groove 11 may form together with the thread slot 12 of the needle 4 a thread duct 13 for receiving the thread, and this can be led out of the thread duct 13 on the open front side thereof.

Figures 6, 6A:
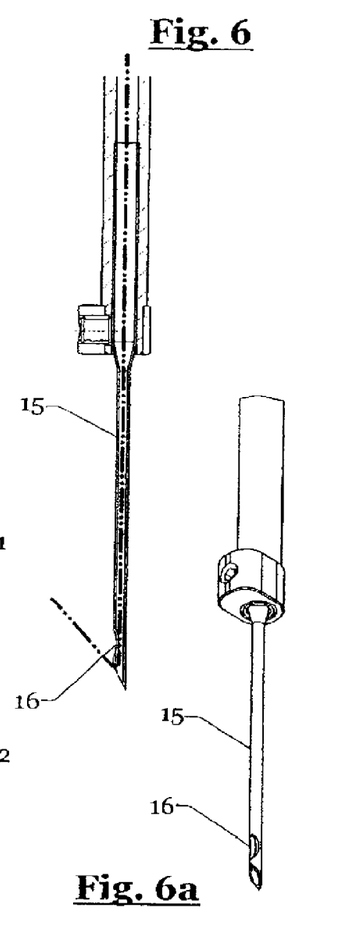
FIG. 6 is a sectional view of a second embodiment of the needle bar and cannula.
FIG. 6a is a front view of the second embodiment of the needle bar and cannula.

In another embodiment of the needle 4 (FIGS. 6 and 6a), this is designed as a cannula 15 and is provided in the area of the thread exit with a lateral recess 16 for the tip of the shuttle 6, as a result of which the reliability with which the needle thread loop is grasped by the shuttle 6 is increased.

To mount the thread reserve, a mounting device 17 (FIGS. 2 and 3) is provided, which is formed by a two-part housing 18 and has a base part 19. A cylindrical mount 21 for a thread spool 23 receiving the thread reserve is formed at the base part 19. The inner wall of the mount 21 encloses the thread spool 23 inserted into said mount, and the diameter of the flanges 24 of the thread spool 23 is slightly smaller—preferably by only a few tenths of one mm—than the internal diameter of the mount 21. It is thus ensured that the thread will not be clamped between the thread spool and the inner wall of the mount 21 even if it should become detached from the thread spool 23. To guide the thread spool 23 within the mount 21, a centering pin 22 is provided in the mount 21, at which pin a ring-shaped contact surface is also formed for the thread spool 23. To minimize the moment of friction of the thread spool 23 when the thread is being pulled off, the external diameter of the contact surface 25 is only slightly larger than the diameter of the hole in the thread spool 23. To close the mounting device 17 and hence the two-part housing 18, a cover 32 is provided, whose shape corresponds to the shape of the base part 19. Cover 32 is detachably connected to the base part 19 by means of a screw connection in the known manner and is removed to insert the filled thread spool 23 into the mount 21.

To obtain and set the thread tension, the thread tensioning means 8, which is essentially formed by two pressure pieces 29, 37 arranged in parallel to one another and one on top of another, is also arranged within the housing 18, and the thread is moved through between these. The pressure pieces 29, 37 may have the shape of small cylindrical rollers, or may be formed by straight pins. To reduce the coefficient of friction, the straight pins may be jacketed with a plastic or consist of a plastic. The pressure pieces 29, 37 lie one on top of another in a non-positive manner, the upper pressure piece 29 lying on the lower pressure piece 37 a non-positive manner. The frictional connection is generated here by a spiral spring 33 lying on the upper pressure piece 29. In case of a corresponding arrangement, the frictional connection may also be generated by a compression spring or tension spring instead of by the spiral spring 33.

To change the force acting on the upper pressure piece 29 and hence to change the retaining force of the thread tensioning means 8, the latter has an adjusting means 34, which acts on the spiral spring 33 between the contact points thereof. The adjusting means 34 is provided with a handle 38 projecting from the housing, so that when said handle is actuated, the spiral spring 33 is deformed and the contact force of the upper pressure piece 29 on the thread located between the pressure pieces 29, 37 is changed correspondingly.

A thread guide 36, which is formed in a simple manner by a pin directed at right angles to the direction in which the thread is pulled off, is provided at the base part 19 of housing 18 for the exit of the thread from the closed mounting device 17. Furthermore, the mount 21, the centering pin 22 arranged in same, as well as the thread guide 36 are arranged such that the thread is pulled off in the use position of the machine essentially in a straight line downwardly.

The thread therefore runs when it is being pulled off at first within the housing 18 from the thread spool 23 over the thread guide 36 between the pressure pieces 29, 37 to a connection piece 35, which is arranged on the lower front side of the housing 18 and attached to the base part 19 thereof. The connection piece 35 is provided at its free end with male threads 46 and has an axially directed hole 39, which extends, on the one hand, up into the interior of the base part 19 for the passage of the thread and opens, on the other hand, into a stepped hole 41. The stepped hole 41 is used to receive a head 42 of a transition piece 43, which is arranged at the upper end of the needle bar 5 and is attached to same. A union nut 44, which cooperates with the external thread 46 of the connection piece 35 and extends behind a collar 45 provided at the transition piece 43 to connect the needle bar 5 to the connection piece 35, is arranged displaceably on the needle bar 5. In the assembled state of the needle bar 5 and connection piece 35, the head 42 connected to the hollow needle bar 5 protrudes into the stepped hole 41 of the connection piece 35, and the hole of said connection piece is aligned with the guide element 9 for the thread, which said guide element is arranged within the hollow needle bar 5.

As a result, the thread runs from the thread spool 23 over the thread guide 36 and the thread tensioning means 8 as well as through the connection piece 35 to the entry into the needle bar 5 and from there to the exit from the needle bar 5 nearly without deflections and thus nearly in a straight line.

Figures 7, 8:
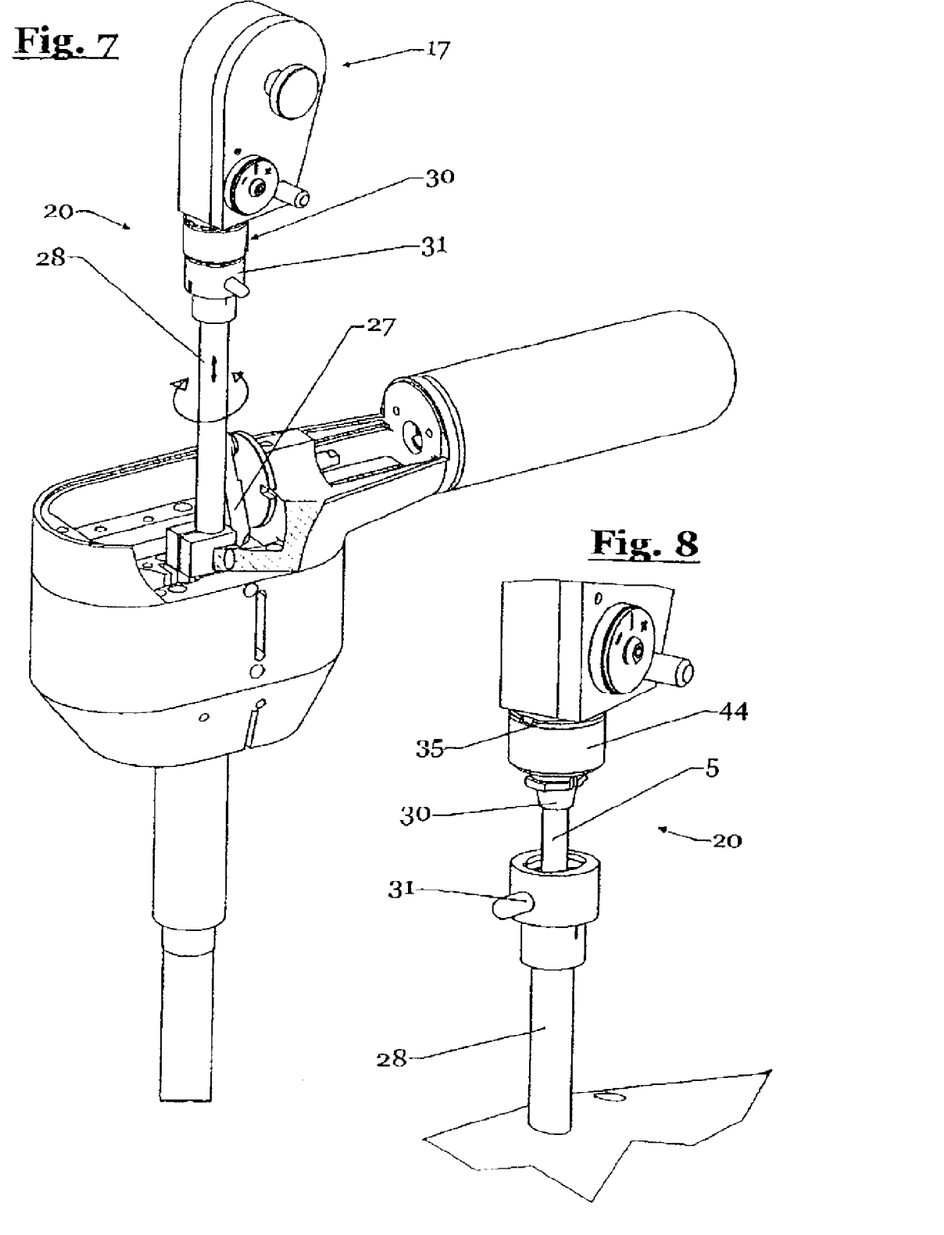
FIG. 7 is a view corresponding to FIG. 1 with the mounting device and bayonet catch.
FIG. 8 is an enlarged view of a detail of the bayonet catch.

The needle bar 5 is arranged within a sleeve 28 driven by a connecting rod 27 and is detachably connected to same. The motion of the connecting rod 27 is derived from the main shaft of the machine. The sleeve 28 is connected for this via a usual revolute joint to the connecting rod 27, while the connection between sleeve 28 and needle bar 5 is formed by a bayonet catch 20, whose fixed part 30 is connected to sleeve 28 and whose loose part 31 is connected to the needle bar 5.

The fixed part 30 of the bayonet catch is adjusted in relation to the hinge point between the connecting rod 27 and sleeve 28 for both the radial and axial adjustment of the needle bar 5. The hinge point between connecting rod 27 and sleeve 28 may be designed for this as a clamping device for receiving the sleeve 28. During mounting, the sleeve 28 is positioned once within this clamping device such that the needle of the needle bar system is in the correct position in terms of its axial and radial positions. If this positioning of the needle is performed correctly with all needle bars, the needle bar 5 can be detached from the machine and removed from same with very little effort by detaching the bayonet catch 20 together with the needle 4 received by it. If the union nut 44 is not detached now, the needle bar 5 and mounting device 17 with thread spool 23 and thread tensioning means 8 can be detached from the machine and removed from same with a single grip only.

The mounting device 17 and needle bar 5 thus form a "needle bar system" receiving both the needle 4 and the thread reserve and the thread tensioning means, which said system is adjusted during its manufacture by means of an adjusting gauge and can be stocked as an immediately ready-to-use assembly unit.

Conversely, the mounting device 17 for the thread spool 23 and thread tensioning means 8 can be filled with a new thread spool 23 outside the machine, the beginning of the thread can be led through the thread tensioning means 8 and connection piece 35 directly up to the head 42 of the needle bar 5 and led from there within the needle bar 5 or within the guide element 9 up to the eye of the needle and also threaded.

Since the adjustment of both the axial and radial positions of the needle bar, which is performed within the framework of the manufacture of the needle thread system, is the same in all needle bar systems and does not change when the needle bar is changed, the needle bar systems thus preassembled can be stocked as a "ready-to-sew unit" and inserted into any machine without any further adjustment and fixed in same with very little effort.

This offers the possibility of stocking "ready-to-sew needle bar systems" equipped with different needles and/or different threads in order to be able to rapidly insert them into the machine when needed and to start suturing.

While specific embodiments of the invention have been shown and described in detail to illustrate the application of the principles of the invention, it will be understood that the invention may be embodied otherwise without departing from such principles.

What is claimed is:

1. An endoscopic suturing machine comprising:
   at least one stitch-forming tool drive;
   a housing with a housing upper part for receiving the least one stitch-forming tool drive;
   stitch-forming tools comprising a thread-carrying needle and a shuttle;
   a transmission means for transmitting the motions generated by the at least one stitch-forming tool drive to the stitch-forming tools;
   a housing shaft adjoining the housing upper part for receiving the transmission means;
   a shuttle bar;
   at least one needle bar for receiving and guiding the thread and guided in the housing shaft with the thread-carrying needle, the shuttle cooperating with the needle to form stitches, the shuttle being received by the shuttle bar, the needle bar comprising a hollow body;
   a mounting device;
   a thread spool receiving a thread reserve, the thread spool being connected to the mounting device; and
   thread guide elements arranged between the thread spool and the needle bar, the thread guide elements being arranged in relation to the needle bar such that the thread runs essentially in a straight line between an exit from the mounting device and an entry into the needle bar.

2. An endoscopic suturing machine in accordance with claim 1, further comprising a guide element passing through the needle bar is arranged for the thread within the needle bar.

3. An endoscopic suturing machine in accordance with claim 1, further comprising a fastening means for the needle wherein in the area of the fastening means for the needle, the needle bar has an exit opening directed outwardly and preferably obliquely downwardly for the thread.

4. An endoscopic suturing machine in accordance with claim 1, further comprising a fastening means for the needle wherein the needle bar has a longitudinal groove to receive the thread in the area of the fastening means for the needle.

5. An endoscopic suturing machine in accordance with claim 4, wherein:
   the needle bar has a longitudinal groove to receive the thread;
   the needle has a flat shank with a thread slot; and
   the longitudinal groove, together with the thread slot of the needle, forms a thread duct and the thread exits from the thread duct on an open front side thereof.

6. An endoscopic suturing machine in accordance with claim 1, wherein the needle comprises a cannula and has a lateral recess for the tip of the shuttle in a rest of an area of a needle eye.

7. An endoscopic suturing machine in accordance with claim 1, wherein the thread reserve is mounted within the mounting device and the mounting device is detachably connected to the needle bar.

8. An endoscopic suturing machine in accordance with claim 7, wherein the mounting device for the thread reserve is formed by a two-part housing including a base part having a cylindrical mount with a centering pin for the thread spool.

9. An endoscopic suturing machine in accordance with claim 8, wherein a contact surface, which has an axial distance from a bottom surface of the mount, is formed for the thread spool at the centering pin.

10. An endoscopic suturing machine in accordance with claim 8, wherein the transmission means is connected to the needle bar by a connection piece, and the connection piece is also used to guide the thread.

11. An endoscopic suturing machine in accordance with claim 10, wherein the connection piece is arranged in relation to the mounting device and the needle bar such that the thread can be inserted without deflections from the mounting device into the connection piece.

12. An endoscopic suturing machine in accordance with claim 7, wherein the internal diameter of the thread spool is only larger than the external diameter of flanges of the thread spool by a few tenths of one mm.

13. An endoscopic suturing machine in accordance with claim 7, wherein:
   the thread tensioning means is arranged within the mounting device for the thread reserve;
   the thread tensioning means is formed by two pressure pieces, arranged in parallel to one another and one on top of another; and
   an upper pressure piece lies on a lower pressure piece in a non-positive manner.

14. An endoscopic suturing machine in accordance with claim 13, wherein a frictional connection is formed by a leaf or compression spring acting on the upper pressure piece.

15. An endoscopic suturing machine in accordance with claim 14, further comprising an adjusting means with a handle arranged outside the housing, the adjusting means being associated with the leaf or compression spring to change a pressing force of the leaf or compression spring.

16. An endoscopic suturing machine in accordance with claim 1, further comprising a detachable connection wherein:
   the needle bar is arranged within a sleeve driven by a connecting rod; and
   the needle bar is detachably connected to the sleeve via the detachable connection.

17. An endoscopic suturing machine in accordance with claim 16, wherein the detachable connection between the sleeve and the needle bar comprises a bayonet catch with a fixed part connected to the sleeve and with a movable part connected to the needle bar.

18. An endoscopic suturing machine comprising:
   at least one stitch-forming tool drive;
   a housing with a housing upper part, said at least one stitch-forming tool drive being arranged in said housing upper part;
   stitch-forming tools comprising a thread-carrying needle and a shuttle;

a transmission means for transmitting movement generated by said at least one stitch-forming tool drive to the stitch-forming tools;

a housing shaft connected to said housing upper part for receiving the transmission means;

a shuttle bar;

at least one needle bar for receiving and guiding thread and guided in the housing shaft with said thread-carrying needle, said at least one needle bar comprising a needle bar opening, said shuttle cooperating with the needle to form stitches, said shuttle being connected to said shuttle bar, said needle bar comprising a hollow body;

a mounting device;

a thread spool receiving a thread reserve, said thread spool being connected to said mounting device; and thread guide elements arranged between the thread spool and the needle bar, at least a portion of said mounting device, said thread guide elements and at least a portion of said needle bar defining a substantially linear line threading path, said substantially linear line threading path extending from an exit of said mounting device to said needle bar opening, wherein the thread extends continuously, without interruption, along said threading path, wherein a portion of the thread extends in a substantially linear line from said exit of said mounting device to said needle bar opening.

19. An endoscopic suturing machine in accordance with claim 18, further comprising a detachable connection wherein:

the needle bar is arranged within a sleeve driven by a connecting rod; and the needle bar is detachably connected to the sleeve via the detachable connection, wherein the detachable connection between the sleeve and the needle bar comprises a bayonet catch with a fixed part connected to the sleeve and with a movable part connected to the needle bar.

20. An endoscopic suturing machine comprising:

at least one stitch-forming tool drive;

a housing with a housing upper part, said at least one stitch-forming tool drive being arranged in said housing upper part;

stitch-forming tools comprising a thread-carrying needle and a shuttle;

a transmission means for transmitting movement generated by said at least one stitch-forming tool drive to the stitch-forming tools;

a housing shaft connected to said housing upper part for receiving the transmission means;

a shuttle bar;

at least one needle bar for receiving and guiding thread and guided in the housing shaft with said thread-carrying needle, said at least one needle bar comprising a needle bar opening, said shuttle cooperating with said needle to form stitches, said shuttle being connected to said shuttle bar, said needle bar comprising a hollow body;

a mounting device;

a thread spool receiving a thread reserve, said thread spool being connected to said mounting device; and thread guide elements arranged between the thread spool and the needle bar, wherein a portion of said thread extends in a substantially straight line from an exit of said mounting device to said needle bar opening, wherein at least a portion of said portion of said thread engages said thread guide elements.

* * * * *